United States Patent
Maus et al.

(10) Patent No.: US 12,398,167 B2
(45) Date of Patent: Aug. 26, 2025

(54) PROCESS FOR PRODUCING METALLOCENES

(71) Applicant: LANXESS Organometallics GmbH, Bergkamen (DE)

(72) Inventors: Silvia Maus, Selm (DE); Bianka Hofmann, Menden (DE); Thorsten Holtrichter-Roessman, Muenster (DE)

(73) Assignee: LANXESS ORGANOMETALLICS GMBH, Bergkamen (DE)

( * ) Notice: Subject to any disclaimer, the term of this patent is extended or adjusted under 35 U.S.C. 154(b) by 628 days.

(21) Appl. No.: 17/426,230

(22) PCT Filed: Jan. 27, 2020

(86) PCT No.: PCT/EP2020/051914
§ 371 (c)(1),
(2) Date: Jul. 28, 2021

(87) PCT Pub. No.: WO2020/156998
PCT Pub. Date: Aug. 6, 2020

(65) Prior Publication Data
US 2022/0081460 A1    Mar. 17, 2022

(30) Foreign Application Priority Data
Jan. 28, 2019 (EP) .................................... 19153951

(51) Int. Cl.
*C07F 17/00* (2006.01)
*C07F 7/00* (2006.01)

(52) U.S. Cl.
CPC .................................. *C07F 17/00* (2013.01)

(58) Field of Classification Search
CPC ......... C07F 17/00; C07F 7/00; C08F 4/65927
See application file for complete search history.

(56) References Cited

U.S. PATENT DOCUMENTS

| | | |
|---|---|---|
| 5,308,811 A | 5/1994 | Suga et al. |
| 5,670,681 A | 9/1997 | Kuber et al. |
| 5,886,202 A * | 3/1999 | Jung ........................ C07F 17/00 556/11 |
| 5,942,586 A | 8/1999 | Herrmann et al. |
| 5,962,719 A * | 10/1999 | Winter .................. C08F 110/06 502/103 |
| 5,968,863 A | 10/1999 | Nifant et al. |
| 6,063,880 A | 5/2000 | Winter et al. |
| 6,072,085 A | 6/2000 | Verdaguer et al. |
| RE37,384 E | 9/2001 | Winter et al. |
| 6,388,118 B1 | 5/2002 | Nifant et al. |
| 6,469,188 B1 | 10/2002 | Miller et al. |
| 2020/0071348 A1 | 3/2020 | Preetz et al. |

FOREIGN PATENT DOCUMENTS

| | | | |
|---|---|---|---|
| EP | 722949 A2 * | 7/1996 | ............. C07C 13/28 |
| GB | 934281 A | 8/1963 | |
| JP | 20010399320 B2 | 6/2008 | |
| JP | 20130252869 A2 | 6/2015 | |

OTHER PUBLICATIONS

D. Johnson et al., 20 Found Chem 15-27 (2018) ("Johnson") (Year: 2018).*
R. Maginn, et al., 85 Journal of the American Chemical Society 672-676 (1963) (Year: 1963).*
C. Goodwin, et al., 139 Journal of the American Chemical Society 18714-18724 (2017) (Year: 2017).*
V. Dang et al., 18 Organometallics 3781-3791 (1999) (Year: 1999).*
N.G. Anderson, Practical Process & Research Development 81-111 (2000) (Year: 2000).*
European Search Report from corresponding European Application No. 19153951, dated May 29, 2019, two pages.
Kaminsky, W., Metalorganic Catalysts for Synthesis and Polymerization pp. 446-464, obtained on Jul. 28, 2021, from the Internet at www.link.springer.com/chapter/10.1007/978-3-642-60178-1_40, Abstract.

* cited by examiner

*Primary Examiner* — Alexander R Pagano
*Assistant Examiner* — Frank S. Hou
(74) *Attorney, Agent, or Firm* — Nicanor A. Kohncke; Christopher L. McDavid; Ewa M. Wozniak

(57) ABSTRACT

The present invention relates to an improved process for the preparation of metallocenes of the general formula (A) $CR_2L_2MX_2$ as well as to intermediates useful in the synthesis of said metallocene and the use thereof as a catalyst in a polymerization of an olefin.

13 Claims, No Drawings

PROCESS FOR PRODUCING METALLOCENES

FIELD OF THE INVENTION

The present invention relates to an improved process for the preparation of metallocenes of the general formula (A) $CR_2L_2MX_2$ as well as to intermediates useful in the synthesis of said metallocene and the use thereof as a catalyst in a polymerization of an olefin.

BACKGROUND OF THE INVENTION

The polymerization of olefins such as ethylene and propylene for manufacturing thermoplastics or norbornene-containing polymers often uses transition metal compounds, particularly metallocene compounds, as a polymerization catalyst. Such polymerization catalysts have been diversely modified and studied over the last decades.

For example, metallocene compounds comprising an unsubstituted or alkyl-substituted indenyl or fluorenyl ligand system are known (GB-A-934,281).

As is generally known in the art, bridged and substituted bis-(1-indenyl) ligands are suitable for use as starting compounds in the process for producing a metallocene catalyst for the polymerization of olefin.

U.S. Pat. No. 6,072,085 discloses 2,2-bisindenylpropane as carbon-bridged substituted biscyclopentadiene compound.

EP-A-0 485 823 and EP-A-0 563 917 discloses zirconium-based metallocenes (so called zirconocenes) comprising bridged indenyl derivatives as ligands.

In Metalorganic Catalysts for Synthesis and Polymerization, 1999, page 462 (Walter Kaminsky), and in EP-A-0 511 665, isopropyliden-bis-(1-indenyl)zirconium dichloride and isopropyliden-bis-(1-fluorenyl)zirconium dichloride are disclosed.

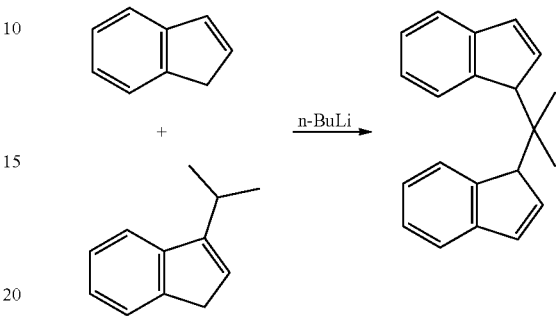

However, there is continuous interest in producing such bridged metallocene compounds with high yield in a more effective way.

EP-A-0 416 566 discloses a process for producing 2,2-bis(1-indenyl)propane. Indene was reacted with n-butyl lithium and afterwards, 1-isopropylindene was added to produce 2,2-bis(1-indenyl)propane.

2,2-bis(1-indenyl)propane was further reacted with n-butyl lithium and afterwards, a zirconium chloride solution in dichloromethane was added to produce isopropyliden-bis-(1-indenyl)zirconium dichloride. The orange precipitate was filtered, washed with dichloromethane and dried. The yield of 2,2-bisindenylpropane was 39%.

EP-A-0 722 949 discloses a process for producing 2,2-bis(1-indenyl)propane. Indene was added to a suspension of potassium hydroxide (KOH) and dimethoxyethane (DME) and acetone was added dropwise. The resulting mixture was treated with diluted phosphoric acid and diethyl ether. The organic phase was separated, washed and dried over $Na_2SO_4$.

EP-A-0 722 950 discloses a process for producing bridged metallocenes such as rac-isopropylidene-bis(indenyl)zirconium dichloride. 2,2-bis(indenyl)propane was dissolved in ether and treated with n-BuLi in pentane. The suspension was treated with triethylstannylchloride and afterwards, $ZrCl_4$ was added to the separated organic phase.

EP-B-0 751 143 discloses a process for producing 2,2-bisindenylpropane and isopropyliden-bis-(1-indenyl)zirconium dichloride. Indene was solved in toluene and an aqueous solution of sodium hydroxide (NaOH) and phase transfer catalyst triethylbenzylammonium chloride (TEBA) was added. Afterwards, acetone was added dropwise. The aqueous phase was separated and two times extracted with diethyl ether. Finally the organic phase was dried over $MgSO_4$ and the solvent was removed under vacuum. The yield of 2,2-bisindenylpropane was 85%.

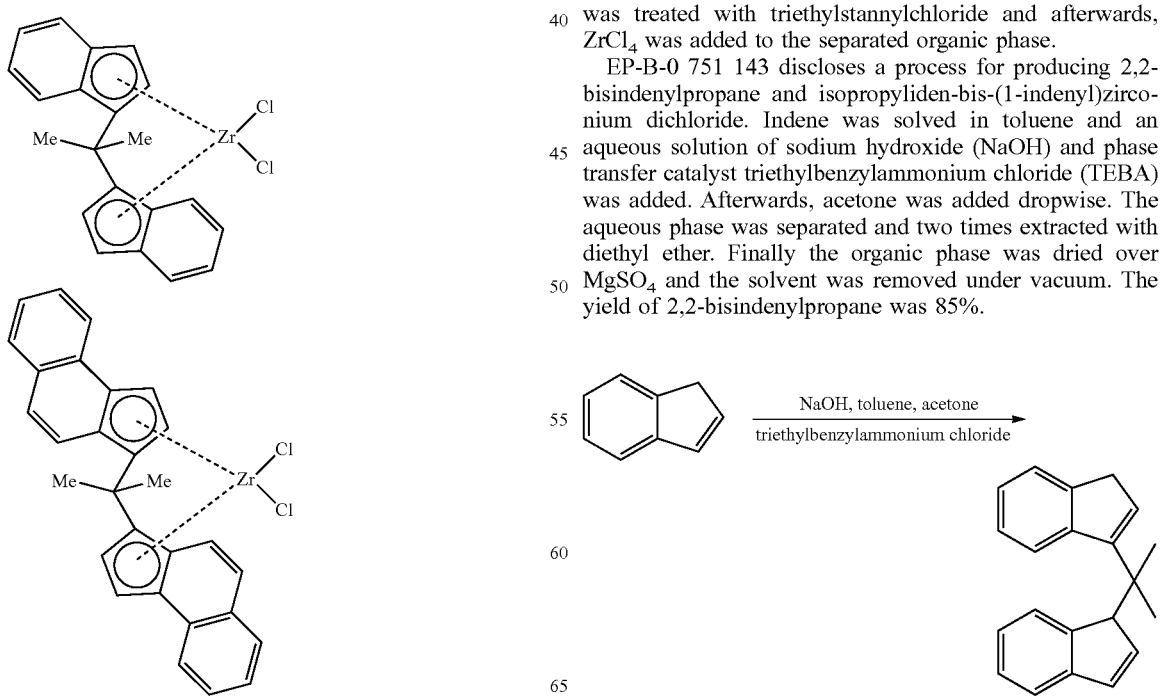

In addition, a metalation step as a next step yielding 55% of the isolated product was disclosed in EP-A-0 751 143. 2,2-bisindenylpropane was reacted in diethyl ether with n-butyl lithium (BuLi). After adding hexane, the suspension was filtered and washed with pentane. The dilithium salt precipitates was dried and added to a suspension of $ZrCl_4$ in dichloromethane.

However, the yield is not satisfying for commercial purposes. Furthermore, traces of the phase transfer catalyst triethylbenzylammonium chloride and impurities remain in the product and interferes with subsequent reactions.

JP4108334 discloses a process for producing 2,2-bisindenylpropane derivatives which have a substituent in position 2 via isopropylidene-bis (2-bromo-1-indene) intermediates and metallocenes thereof, e.g. isopropylidene-bis (2-methyl-1-indenyl) zirconium dichloride.

As described above, there have been many studies on metallocene compounds as a catalyst for producing olefin polymer and processes for producing the same. Despite the progress which has been described hitherto, there still is room left for improving a process for producing metallocene catalysts. In particular, in order to establish the synthesis route that can easily be scaled up, it is essential to have a reproducible synthesis route and process.

Besides being reproducible a production process is sought that is efficient in the conversion of starting materials, in the usage of solvents and catalysts, and in the number of synthesis steps, i.e. a process that is economic.

SUMMARY OF THE INVENTION

As outlined above, the object of the present invention to be solved can be seen in providing an improved process for producing metallocenes of the general formula (A) $CR_2L_2MX_2$ such as isopropylidene bis-(1-indenyl) zirconium dichloride.

The present invention provides a process for preparing metallocenes of the general formula (A)

$$CR_2L_2MX_2 \quad (A)$$

comprising the steps of:
(a) reacting a symmetric or asymmetric, linear or cyclic ketone of the general formula (B) (C=O)$R_2$ and ligand L in the presence of an alkali metal alkoxide $M^1OR^1$ so as to form a compound of the general formula (C) $CR_2L_2$; and
(b) reacting said compound (C) $CR_2L_2$ with metal halide $MX_4$ in the presence of a deprotonation agent, whereas
R is individually $C_1$-$C_8$ alkyl, cycloalkyl or phenyl, preferably methyl, ethyl, propyl or phenyl, more preferably methyl or phenyl,
$R^1$ is $C_1$-$C_{20}$ alkyl, preferably $C_1$-$C_6$ alkyl, more preferably methyl or ethyl,
L is individually unsubstituted indenyl, substituted indenyl, unsubstituted benzoindenyl, substituted benzoindenyl, unsubstituted fluorenyl or substituted fluoreny, preferably unsubstituted indenyl, unsubstituted fluorenyl or unsubstituted benzoindenyl and more preferably unsubstituted indenyl,
M is zirconium, hafnium, titanium or a lanthanide, preferably zirconium or hafnium, more preferably zirconium,
$M^1$ is an alkali metal, preferably lithium, sodium or potassium, more preferably sodium and
X is halogen, preferably chlorine or bromine, more preferably chlorine.

Furthermore, the present invention provides use of metallocenes of the general formula (A) obtained according to the present invention as a catalyst in a polymerization of an olefin.

These and further features and advantages of the present invention will be apparent from the following detailed description and claims.

DETAILED DESCRIPTION OF THE INVENTION

Throughout this specification and the claims or items, unless the context requires otherwise, the word "comprise" and variations such as "comprises" and "comprising" will be understood to imply the inclusion of a stated integer (or step) or group of integers (or steps).

The present invention is directed to a process for producing metallocenes of the general formula (A) $CR_2L_2MX_2$, preferably isopropylidene bis-(1-indenyl) zirconium dichloride.

Furthermore, the present invention provides a use of said metallocenes of the general formula (A) $CR_2L_2MX_2$, preferably isopropylidene bis-(1-indenyl) zirconium dichloride, as a polymerization catalyst for olefins.

Reaction Step (a)—Preparation of the Compound of the General Formula (C) $CR_2L_2$ The process for producing metallocenes of the general formula (A) $CR_2L_2MX_2$ such as isopropylidene bis-(1-indenyl) zirconium dichloride comprises a first step (a), wherein a symmetric or asymmetric, linear or cyclic ketone of the general formula (B) (C=O)$R_2$ and a ligand L are reacted in the presence of sodium methoxide or sodium ethoxide so as to form a compound of the general formula (C) $CR_2L_2$.

Ketone (B) (C=O)$R_2$

The ketone of the general formula (B) (C=O)$R_2$ is a symmetric or asymmetric, linear or cyclic ketone, whereas R is individually $C_1$-$C_8$ alkyl, cycloalkyl or phenyl, preferably methyl, ethyl, propyl or phenyl, more preferably methyl or phenyl. R can be connected to form a 3-7-membered cyclic ring.

In a preferred embodiment, the keton (B) is acetone, benzophenone, acetobenzophenone or cyclohexanone, more preferably acetone or benzophenone.

Ligand L

The ligand L is individually unsubstituted indenyl, substituted indenyl, unsubstituted benzoindenyl or substituted benzoindenyl, preferably unsubstituted indenyl, unsubstituted fluorenyl or unsubstituted benzoindenyl and more preferably unsubstituted indenyl.

In the present invention, the word "substituted" means $C_1$-$C_{20}$ alkyl substituted or $C_1$-$C_{20}$ aryl substituted.

Preferred examples of substituted indenyl ligands are 4,5,6,7-tetrahydro-1-indene, 3-methylindene, 3-tert-butylindene, 3-trimethylsilylindene or 4-phenylindene.

Preferred examples of substituted benzoindenyl ligands are 4,5-benzoindene, 2-methyl-4,5-benzoindene, 2-methyl-α-acenaphthindene or 2-methyl-4,6-diisopropylindene.

In a preferred embodiment of the present invention, only one type of ligand L is used in reaction step (a) and no mixtures.

Alkali Metal Alkoxide $M^1OR^1$

The first reaction step (a) of the present invention is performed in the presence of an alkali metal alkoxide $M^1OR^1$, wherein $R^1$ is $C_1$-$C_{20}$ alkyl, preferably $C_1$-$C_6$ alkyl, more preferably methyl or ethyl, most preferably methyl and $M^1$ is an alkali metal, preferably lithium, sodium or potassium, more preferably sodium.

In a preferred embodiment, the reaction if performed in the presence of alkali metal methoxide or alkali metal ethoxide. In a more preferred embodiment, the reaction is performed in the presence of sodium methoxide or sodium ethoxide. In the most preferred embodiment, the reaction is performed in the presence of sodium methoxide.

In a preferred embodiment, the reaction of the first reaction step (a) comprises the reaction of acetone with sodium methoxide and unsubstituted indene in dimethylsulfoxide (DMSO) and can be summarized as follows:

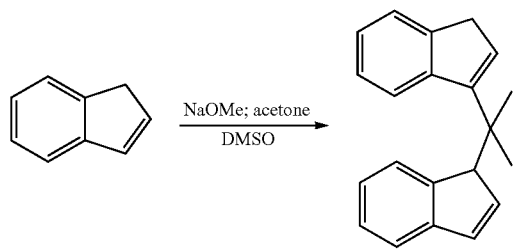

In a preferred embodiment of the invention, the compound of the general formula (C) is 2,2-bisindenylpropane.

According to the present invention it was found that by using sodium methoxide or sodium ethoxide as a base in the first reaction step, the formation of compounds of the general formula (C) $CR_2L_2$, preferably of the intermediate 2,2-bisindenylpropane, can be achieved in much higher yield and in the absence of side products such as indenylsodium, oxidation products of indenylsodium or polymerization products, which are usually obtained when using alkali metal hydroxide such as sodium hydroxide or potassium hydroxide as a base.

Especially, when using sodium hydroxide it was found that the yield of the intermediate 2,2-bisindenylpropane varied drastically and in some test reactions even did not produce any 2,2-bisindenylpropane product. Furthermore, when using sodium hydroxide it was difficult and/or cumbersome to remove the side products from the desired product, i.e., 2,2-bisindenylpropane.

Furthermore, according to the present invention it was found that when using dimethylformamide (DMF) or dimethylsulfoxide (DMSO) as a solvent in the reaction of symmetric or asymmetric, linear or cyclic ketone and indene, high product yields of 2,2-bisindenylpropane of for example more than 60% of isolated product, more preferably of more than 70% could be obtained.

In an even more preferred embodiment the reaction of symmetric or asymmetric, linear or cyclic ketone (B) and indene is carried out by adding symmetric or asymmetric, linear or cyclic ketone (B) to a reaction mixture comprising indene and dimethylformamide (DMF) or dimethylsulfoxide (DMSO), preferably DMSO.

In an even more preferred embodiment the reaction of symmetric or asymmetric, linear or cyclic ketone (B) and ligand L as described above is carried out at temperatures of 0 to 40° C., more preferably 0 to 25° C., even more preferably 5 to 15° C. for a time period of 10 minutes to 30 minutes.

In a preferred embodiment, the reaction mixture is additionally stirred for 1 to 120 minutes at less than 40° C.

After running this reaction, usually the reaction mixture is worked up for example by adding methyl-tert-butyl ether (MTBE) and/or water and/or 10% NaCl solution so as to quench the reaction mixture, separate the organic phase by phase separation and washing the organic phase with water. Thereafter, usually the organic phase is dried for example by adding sodium sulfate ($Na_2SO_4$). Subsequently the organic phase may be subjected to a distillation step so as to purify the product 2,2-bisindenylpropane.

In a preferred embodiment, the reaction of step (a) is performed in the absence of any phase transfer catalyst.

As shown above, according to the present invention thereafter the second reaction step (the "metalation") is carried out.

Reaction Step (b)—Preparation of the Metallocene of the General Formula (A) $CR_2L_2MX_2$ In a second step (b) of the process of the invention, said compound of the general formula (C) $CR_2L_2$ is reacted with metal halide $MX_4$ in the presence of a deprotonation agent so as to form metallocenes of the general formula (A) $CR_2L_2MX_2$, preferably isopropylidene bis-(1-indenyl) zirconium dichloride.

Metal Halide $MX_4$

X of the metal halide $MX_4$ is a halogen, preferably fluoride, chloride, bromide or iodide, more preferably chloride.

M of the metal halide $MX_4$ is zirconium (Zr), hafnium (Hf), titanium (Ti) or a lanthanide like neodymium.

The metal halide $MX_4$ is preferably $ZrF_4$, $ZrCl_4$, $ZrBr_4$, $ZrI_4$, $HfCl_4$, $TiCl_4$ or $NdCl_3$, more preferably $ZrCl_4$.

Deprotonation Agent

In the present invention, a typical deprotonation agent can be used. Preferably, the deprotonation agent is butyl lithium (n-BuLi), sodium hydride (NaH), BEM or BOMAG, more preferably n-BuLi. In a preferred embodiment, a deprotonation agent is used which is highly soluble in tetrahydrofuran (THF).

In a preferred embodiment of the present invention said second reaction step (b) is carried out by using tetrahydrofuran (THF), methyl-tert-butyl ether (MTBE), ethyl tert-butyl ether (ETBE), tert-amyl methyl ether (TAME), methyl tetrahydrofuran, di-n-butyl ether or diisopropyl ether (DIPE), more preferably a mixture of THF and hexane as a solvent.

In a preferred embodiment of the present invention said second step (b) is carried out by using n-BuLi solution in hexane with a concentration of 80% or more, preferably with a concentration of 90% or more. n-BuLi concentrations of less than 80% such as commercial available solutions of only 20% are not preferred as the amount of hexane gets high which causes precipitation of LiCl.

In a preferred embodiment, the ligand L is solved first in a solvent, preferably in THF, MTBE, ETBE, TAME or DIPE, and afterwards, the deprotonation agent and metal halide $MX_4$ are added to the mixture.

1. Step

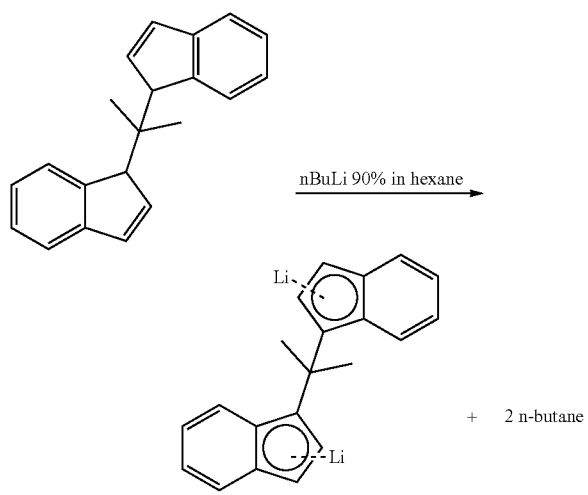

2. Step

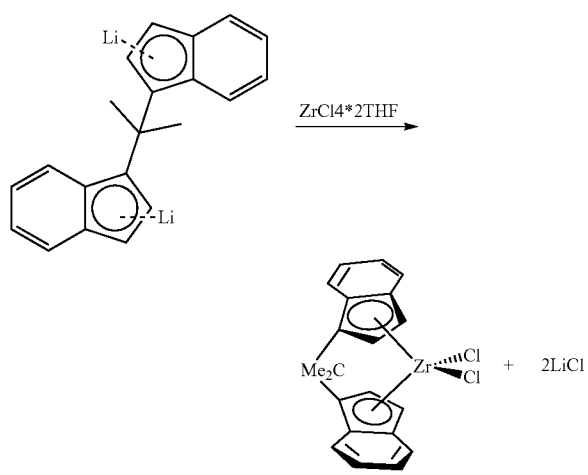

Usually said second reaction step (b) is carried out by adding $MX_4$ to the compound (C) $CR_2L_2$, at temperatures of 0 to −20°, more preferably −5 to −15° C. for a time period of 15 minutes to 10 hours, more preferably 30 minutes to 5 hours.

Preferably said second reaction step (b) is carried out by adding zirconium(IV) chloride to the intermediate dilithium salt of 2,2-bisindenylpropane, at temperatures of 0 to −20°, more preferably −5 to −15° C. for a time period of 15 minutes to 10 hours, more preferably 30 minutes to 5 hours.

The present inventors found that high yields of the final product can be achieved by using THF in the second reaction step as the solvent because in said case, the by-product LiCl formed in the second reaction step, does not have to be removed in an additional step, as it is soluble in THF whereas the product is not and thus, precipitates.

As known in the art, the polymerization yield of an olefin in the presence of a metallocene catalyst such as isopropylidene bis-(1-indenyl) zirconium dichloride, depends on the purity of the metallocene catalyst. When using isopropylidene bis-(1-indenyl) zirconium dichloride obtained according to the process claimed in the present invention, as metallocene catalyst in the polymerization of an olefin, surprisingly a high polymerization yield could be achieved.

In a preferred embodiment of the present invention, the metallocenes of the general formula (A) $CR_2L_2MX_2$, are symmetrical.

According to a further aspect of the present invention, metallocenes of the general formula (A), preferably isopropylidene bis-(1-indenyl) zirconium dichloride, produced according to any process of the present invention, is used as a catalyst in a polymerization of an olefin.

EXAMPLES

Example 1

Reaction Step (a) Synthesis of 2,2-Bisindenylpropane

All manipulations were carried out under inert gas atmosphere (argon). A double wall reactor of 2 L volume was charged with DMSO (100 mL), NaOMe (0.9 g, 0.02 mol) and indene (40 g, 0.33 mol) and stirred for 30 minutes at 20° C. The reactor was cooled to 10° C. Then, acetone (9.7 g, 0.17 mol) was added within 15 minutes so that the reactor temperature remains below 20° C. (exothermic reaction). Afterwards, the reaction mixture was stirred for 2 h at 40° C. and overnight at room temperature until the reaction was complete (as judged by GC, 6,6-dimethylfulvene<1%). At 10° C. 100 g water were added and stirred for 30 minutes, than Methyl-tert-butyl ether (MTBE; 236 g) was added to the reaction mixture. The mixture was stirred at room temperature for additional 30 minutes The two phases were separated, the water phase again extracted with MTBE and the combined organic phases were washed neutral with a saturated NaCl solution water (2×100 mL). The organic phase was dried over $Na_2SO_4$ and then MTBE and unconverted indene were removed by vacuum distillation at max. 40° C. almost to dryness. The remaining thick suspension was filtered and the crude product washed with methanol, hexane and MTBE. Drying yielded a brown, crystalline solid with a purity of 98.4% (27 g) Additional workup of the remaining mother liquids similar to the isolation step described resulted in additional 10 g pure product. Total yield 37 g, 81%.

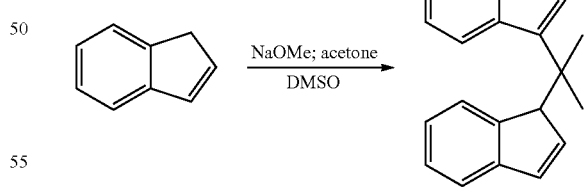

Reaction Step (b) Preparation of Isopropylidene Bis-(1-Indenyl)Zirconium Dichloride All manipulations were carried out under inert gas atmosphere. In a double wall reactor of 2 L volume 2,2-bisindenylpropane (15.8 g, 0.056 mol, purity 98.6% of reaction step (a) was dissolved in tetrahydrofuran (THF; 200 mL) at room temperature and the mixture was cooled to −5° C. Within 30 min n-BuLi (90% solution in n-hexane, 8.06 g, 0.1120 mol)

were added so that the reactor temperature remains below 7° C. The solution was stirred for 60 min at 0° C. The dilithium salt of the ligand precipitates. The suspension is warmed to room temperature and stirred at 25° C. for another 120 min. The, the solution was again cooled to 0° C. and ZrCl$_4$*2THF (21.15 g, 0.056 mol) was added. The addition was exothermic with a temperature increase of ca. 10-20 K. The reaction mixture is warmed to 20° C. and stirred overnight. The dark red product precipitates after 120 minutes. The product is separated by filtration and washed twice with THF and twice with hexane/THF to remove residual traces of LiCl. The product is dried in vacuum yielding 16.6 g (0.038 mol, 67.8% of fine orange to red crystals.

1. Step

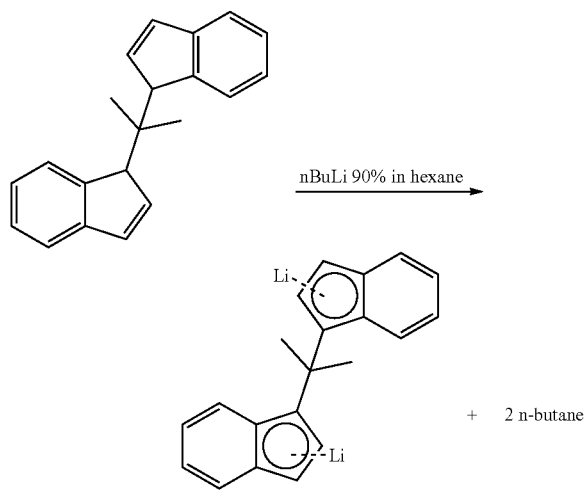

2. Step

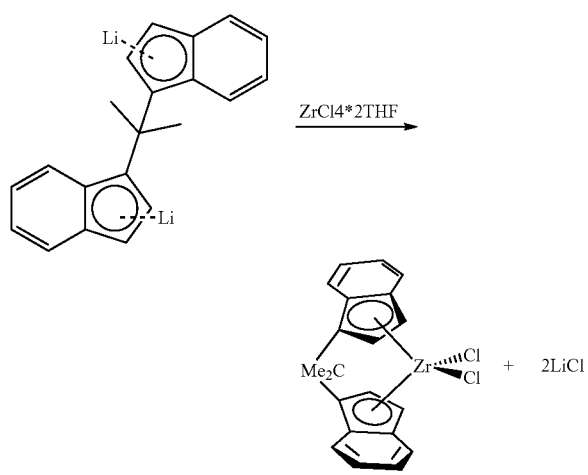

Example 2

The example 2 was performed identically to example 1 with the exemption that the bridge was replaced by benzophenone (O=CPh$_2$; 15.2 g, 0.08 mol) as shown in table 1 and that the amount of NaOMe was doubled. The product is dried in vacuum yielding 35.5 g (0.064 mol, 80.1% i.y) of fine orange to red crystals.

Example 3

Example 3 was performed identically to example 1 with the exception that DMF (dimethyl formamide) was used as a solvent as shown in table 1. The product was dried in vacuum yielding 20.0 g (0.073 mol, 44.2%) of fine white crystals.

Example 4 (Scale Up)

A reactor with a volume of one cubic meter was conditioned with inert gas atmosphere and DMSO (120 kg, 1536 mol) and NaOMe (1.01 kg, 20 mol) were added into the reactor. To the stirred suspension 42.4 kg indene was added and the reaction mixture stirred for 30 minutes at 20° C. The mixture was cooled to 10° C. and acetone (10.6 kg, 180 mol) added within 10 minutes. The reactor was further cooled to keep the temperature below 40° C.

After the addition was completed the reaction mixture was heated to 40° C. and stirred for 1 hour at that temperature. After sampling the reaction mixture was cooled to 20° C. and stirred for 12 hours at 20° C. To the reaction mixture 258 kg MTBE were added followed by the exothermic addition of 118 kg of a 10% NaOH solution at 0° C. The temperature raised to around 20° C. and the resulting biphasic mixture was stirred for min. 30 minutes. The phases were separated, the organic phase again washed with 120 kg MTBE, the combined organic phases dried with Na$_2$SO$_4$ and poured back into the reactor. At 40° C. app. 85% of the MTBE were distilled off, the same amount heptane added and again distilled. The remaining suspension was cooled to 20° C., filtered through a pressure filter and washed with a 1:1 mixture of methanol/heptane. The product was dried in vacuo to yield 30 kg (110.1 mol, 59.4%) of a brownish powder with a purity of more than 96%.

TABLE 1

| Metallocene ligand composition | | | | | | |
|---|---|---|---|---|---|---|
| Nr. | L1 | L2 | Bridge | NaOMe | Solvent | Yield |
| 1 | Ind | Ind | O=CMe$_2$ | 0.05 Eq. | DMSO | 67.8% |
| 2 | Ind | Ind | O=CPh$_2$ | 0.1 Eq. | DMSO | 80.1% |
| 3 | Ind | Ind | O=CMe$_2$ | 0.05 Eq. | DMF | 44.2% |
| 4 | Ind | Ind | O=CMe$_2$ | 0.05 Eq. | DMSO | 59.4% |

Ind = indenyl ligand
O=CMe$_2$ = acetone
O=CPh$_2$ = benzophenone

What is claimed is:

1. A process for preparing a metallocene of the general formula (A)

$$CR_2L_2MX_2 \qquad (A)$$

comprising the steps of:
(a) reacting a symmetric or asymmetric, linear or cyclic ketone of the general formula (B) (C=O)R$_2$ and ligand L in the presence of an alkali metal alkoxide M$^1$OR$^1$ so as to form a compound of the general formula (C) CR$_2$L$_2$ in dimethylsulfoxide; and
(b) reacting said compound (C) CR$_2$L$_2$ with metal halide MX$_4$ in the presence of a deprotonation agent, wherein the deprotonation agent is an n-BuLi solution in hexane with a concentration of 80% or more,
whereas
R is individually C$_1$-C$_8$ alkyl, cycloalkyl or phenyl,
R$^1$ is C$_1$-C$_{20}$ alkyl, L is individually unsubstituted indenyl, substituted indenyl, unsubstituted benzoindenyl, substituted benzoindenyl, M is zirconium, hafnium, titanium or a lanthanide, $M^1$ is an alkali metal, and X is halogen.

2. The process according to claim 1, wherein the ketone (B) is a symmetric ketone.

3. The process according to claim 1, wherein the keton (B) is acetone, benzophenone, acetobenzophenone or cyclohexanone.

4. The process according to claim 1, wherein the alkali metal alkoxide is alkali metal methoxide or alkali metal ethoxide.

5. The process according to claim 1, wherein said reaction step (a) is carried out at a temperature of 0 to 40° C.

6. The process according to claim 1, wherein said reaction step (a) is carried out in the absence of any phase transfer catalyst.

7. The process according to claim 1, wherein said reaction (b) is carried out in tetrahydrofuran, methyl-tert-butyl ether, ethyl tert-butyl ether, tert-amyl methyl ether or diisopropyl ether, or in a mixture of tetrahydrofuran and hexane as a solvent.

8. The process according to claim 1, comprising the steps of:
  (a) reacting acetone and unsubstituted indene in the presence of an sodium methoxide so as to form 2,2-bisindenylpropane; and
  (b) reacting 2,2-bisindenylpropane with $ZrCl_4$ in the presence of n-BuLi solution in hexane with a concentration of 80% or more.

9. The process according to claim 1, wherein

R is methyl, ethyl, propyl or phenyl, $R^1$ is C1-C6 alkyl,

L is individually unsubstituted indenyl or unsubstituted benzoindenyl,

M is zirconium or hafnium, $M^1$ is lithium, sodium or potassium and

X is chlorine or bromine.

10. The process according to claim 1, wherein

R is methyl or phenyl, $R^1$ is methyl or ethyl,

L is individually unsubstituted indenyl,

M is zirconium, $M^1$ is sodium and

X is chlorine.

11. The process according to claim 1, wherein the keton (B) is acetone or benzophenone.

12. The process according to claim 1, wherein the alkali metal alkoxide is sodium methoxide or sodium ethoxide.

13. The process according to claim 1, wherein the reaction (a) is carried out at a temperature of 0 to 25° C. for a time period of 10 minutes to 30 minutes.

* * * * *